(12) United States Patent
Forsman et al.

(10) Patent No.: US 9,409,919 B2
(45) Date of Patent: Aug. 9, 2016

(54) PROCESS FOR THE MANUFACTURE OF SPIROCYCLIC SUBSTITUTED BENZOFUROQUINOLIZINES

(71) Applicant: Vetcare Oy, Salo (FI)

(72) Inventors: Jonas Forsman, Turku (FI); Oili Kallatsa, Turku (FI)

(73) Assignee: VETCARE OY, Salo (FI)

( * ) Notice: Subject to any disclaimer, the term of this patent is extended or adjusted under 35 U.S.C. 154(b) by 0 days.

(21) Appl. No.: 14/969,664

(22) Filed: Dec. 15, 2015

(65) Prior Publication Data

US 2016/0168163 A1    Jun. 16, 2016

(30) Foreign Application Priority Data

Dec. 16, 2014 (FI) ..................... 20146104

(51) Int. Cl.
*C07D 491/22* (2006.01)
*C07D 491/12* (2006.01)
*B01J 25/02* (2006.01)

(52) U.S. Cl.
CPC ............... *C07D 491/22* (2013.01); *B01J 25/02* (2013.01)

(58) Field of Classification Search
USPC .............................................. 546/18, 20, 62
See application file for complete search history.

(56) References Cited

U.S. PATENT DOCUMENTS 4,942,235 A    7/1990    DeCamp et al.

OTHER PUBLICATIONS

Sacchetti et al., "Addition of TMSCN to chiral ketimines derived from isatin. Synthesis of an oxindole-based peptidomimetic and a bioactive spirohydantoin", Organic & Biomolecular Chemistry, 2011, vol. 9, No. 15, pp. 5515-5522, Scheme 4, p. 5517 last chapter-p. 5518 first chapter.
Search Report issued in Finnish priority application No. 20146104, dated Jul. 23, 2015.

*Primary Examiner* — Charanjit Aulakh
(74) *Attorney, Agent, or Firm* — Birch, Stewart, Kolasch & Birch, LLP

(57) ABSTRACT

The present invention relates to a process for the manufacture of N-(2-((2R,12bS)-2'-oxo-1,3,4,6,7,12b-hexahydrospiro[benzofuro[2,3-a]quinolizine-2,4'-imida-zolidine]-3'-yl)ethyl)-methanesulfonamide, where in the process trimethylsilyl cyanide is used.

20 Claims, 2 Drawing Sheets

PROCESS FOR THE MANUFACTURE OF SPIROCYCLIC SUBSTITUTED BENZOFUROQUINOLIZINES

FIELD OF THE INVENTION

The present invention relates to an improved process for the manufacture of spirocyclic substituted benzofuroquinolizines. The present invention relates particularly to a process for the manufacture of N-(2-((2R,12bS)-2'-oxo-1,3,4,6,7,12b-hexahydrospiro[benzofuro-[2,3-a]quinolizine-2,4'-imidazolidine]-3'-yl)ethyl)-methanesulfonamide.

BACKGROUND OF THE INVENTION

The compound N-(2-((2R,12bS)-2'-oxo-1,3,4,6,7,12b-hexahydrospiro[benzofuro[2,3-a]-quinolizine-2,4'-imidazolidine]-3'-yl)ethyl)-methanesulfonamide is a peripherally acting selective $\alpha_2$-adrenoceptor antagonist, known also by codes of MK-467 and L-659,066. It has the chemical formula I presented below, as hydrochloride salt.

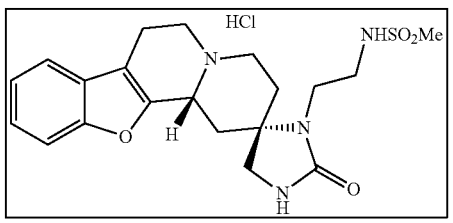

Several processes have been proposed in the art for the manufacture of the compound N-(2-((2R,12bS)-2'-oxo-1,3,4,6,7,12b-hexahydrospiro[benzofuro[2,3-a]-quinolizine-2,4'-imida-zolidine]-3'-yl)ethyl)-methanesulfonamide.

EP 0259092 discloses a five-step process where, in the first step acetylethylenediamine is reacted with methanesulfonyl chloride to obtain 2-methanesulfonylaminoethylacetamide. In the second step 2-methanesulfonylaminoethylacetamide is treated with hydrochloric acid to obtain 2-(aminoethyl)methanesulfonamide. In the third step (12bS)-1,3,4,6,7,12b-hexahydrobenzo[b]furo[2,3-a]quinolizin-2-one is allowed to react with 2-(amino-ethyl)methanesulfonamide, followed by treating with diethyl cyanophosphonate to obtain the intermediate (2R,12bS)-2-cyano-2-(2-methanesulfonamidoethyl)amino-1,3,4,6,7,12b-hexahydrobenzo[b]-furo[2,3-a]-quinolizine. In the fourth step (2R,12bS)-2-cyano-2-(2-methanesulfonamidoethyl)amino-1,3,4,6,7,12b-hexahydrobenzo[b]-furo[2,3-a]-quinolizine is reduced using lithium aluminum hydride to obtain the intermediate (2R,12bS)-2-amino-methyl-2-(2-methanesulfonamidoethyl)amino-1,3,4,6,7,12b-hexahydrobenzo[b]furo[2,3-a]-quinolizine, which is treated in the fifth step with 1,1'-carbonyldiimidazole to obtain the product N-(2-((2R,12bS)-2'-oxo-1,3,4,6,7,12b-hexahydrospiro[benzofuro[2,3-a]-quinolizine-2,4'-imidazoli-dine]-3'-yl)ethyl)-methanesulfonamide, which is converted to the corresponding hydrochloride salt. The starting material (12bS)-1,3,4,6,7,12b-hexahydrobenzo[b]furo[2,3-a]quinolizin-2-one was obtained from the corresponding rasemic compound using acylated L-tartaric acid, such as di-para-toluoyl-L-tartaric acid. This process of EP 0259092 contains several steps and many of them are not suitable for manufacture on a larger industrial scale. Chromatographic methods used for purification are not regarded as appropriate methods on larger scale. In the third step the aminocyanation is carried out using diethyl cyanophosphonate, whereby large amounts of salts are formed and complicated measures are needed for isolating the formed intermediate, whereby losses are typically about 15% or even higher and impurities are formed. Additionally, the salts are regarded as problem waste, which is costly to discard. Further, the reaction is slow, typically it takes about 3 days, which results in increase of the undesired diastereomer and decreases the yield too. Diethyl cyanophosphonate is an expensive reagent and its availability is poor. The use of lithium aluminum hydride in the reduction in the fourth step is hazardous and not suitable for industrial scale.

U.S. Pat. No. 4,942,235 describes an improved process where (2R,12bS)-2-cyano-2-(2-methane-sulfonamido-ethyl)amino-1,3,4,6,7,12b-hexahydrobenzo[b]-furo[2,3-a]-quinolizine, the intermediate obtained in third step of the process of EP 0259092, is first allowed to react with 1,1'-carbonyldiimidazole in the presence of 1,8-diazabicyclo[5.4.0]undec-7-ene to obtain (2R,12bS)-1,3,4,6,7,12b-hexahydro-[2,3-methylsulfonyl)-2-oxo-1-imidazolidinyl]-2H-benzo-furo[2,3-a]quinolizine-2-carbonitrile, which is reduced with hydrogen in the presence of Raney nickel to obtain N-(2-((2R,12bS)-2'-oxo-1,3,4,6,7,12b-hexahydrospiro[benzofuro[2,3-a]-quinolizine-2,4'-imidazolidine]-3'-yl)ethyl)methanesulfonamide, which is converted to the corresponding hydrochloride with a mixture of acetyl chloride and methanol.

There is an evident need for an improved process for the manufacture of spirocyclic substituted benzofuroquinolizines, particularly N-(2-((2R,12bS)-2'-oxo-1,3,4,6,7,12b-hexa-hydrospiro[benzofuro[2,3-a]quinolizine-2,4'-imidazolidine]-3'-yl)ethyl)-methanesulfonamide.

SUMMARY OF THE INVENTION

An object of the invention is to provide an improved process for the manufacture of spirocyclic substituted benzofuroquinolizines, particularly N-(2-((2R,12bS)-2'-oxo-1,3,4,6,7,12b-hexahydrospiro[benzofuro[2,3-a]quinolizine-2,4'-imidazolidine]-3'-yl)ethyl)-methanesulfonamide.

Another object of the invention is to provide an improved process for the manufacture of spirocyclic substituted benzofuroquinolizines, particularly N-(2-((2R,12bS)-2'-oxo-1,3,4,6,7,12b-hexahydrospiro[benzofuro[2,3-a]quinolizine-2,4'-imidazolidine]-3'-yl)ethyl)-methanesulfonamide, which process is suitable for industrial scale.

Another object of the invention is to provide an improved process for the manufacture of spirocyclic substituted benzofuroquinolizines, particularly N-(2-((2R,12bS)-2'-oxo-1,3,4,6,7,12b-hexahydrospiro[benzofuro[2,3-a]quinolizine-2,4'-imidazolidine]-3'-yl)ethyl)-methanesulfonamide, where the use of diethyl cyanophosphonate can be avoided.

The present invention relates to a process for the manufacture of N-(2-((2R,12bS)-2'-oxo-1,3,4,6,7,12b-hexahydrospiro[benzofuro[2,3-a]quinolizine-2,4'-imidazolidine]-3'-yl)ethyl)-methanesulfonamide having the formula I, which process comprises the steps, where in the first step (S)-1,3,4,6,7,12b-hexahydro-2H-benzo[b]furo[2,3-a]quinolizin-2-one of formula II and N-(2-aminoethyl)methanesulfonamide of formula III are contacted with trimethylsilyl cyanide in the presence of an agent capable of capturing water molecules, in an organic solvent, followed by adding hydrogen chloride to obtain (2R,12bS)-[2-[(cyano-1,3,4,6,7,12b-hexahydrobenzofuro-[2,3-a]quinolizine-2-yl)-amino]ethyl]methane-sulfon-amide dihydrochloride, in the second step (2R,12bS)-[2-[(cyano-1,3,4,6,7,12b-hexahydrobenzofuro-[2,3-a]quinolizine-2-yl)-amino]-ethyl]

methanesulfonamide dihydrochloride is contacted with 1,1'-carbonyldiimidazole in the presence of a hydrogen chloride acceptor in an organic solvent to obtain (2R,12bS)-1,3,4,6,7,12b-hexahydro-[2,3-methylsulfonyl)-2-oxo-1-imidazolidinyl]-2H-benzo-furo[2,3-a]quinolizine-2-carbonitrile, and in the third step (2R,12bS)-1,3,4,6,7,12b-hexahydro-[2,3-methylsulfonyl)-2-oxo-1-imidazolidinyl]-2H-benzofuro[2,3-a]quinolizine-2-carbonitrile is contacted with hydrogen in the presence of Raney nickel catalyst and sodium methoxide or potassium tert-butoxide in methanol solvent to yield N-(2-((2R,12bS)-2'-oxo-1,3,4,6,7,12b-hexa-hydrospiro[benzofuro[2,3-a]quinolizine-2,4'-imidazolidine]-3'-yl)ethyl)-methanesulfonamide.

Particularly the present invention relates to a process for the manufacture of N-(2-((2R,12bS)-2'-oxo-1,3,4,6,7,12b-hexahydrospiro[benzofuro[2,3-a]quinolizine-2,4'-imida-zolidine]-3'-yl)ethyl)-methanesulfonamide, where in the first step the aminocyanation step is carried out using trimethylsilyl cyanide.

The process of the invention is described in the following exemplary scheme 1.

Synthetic Route

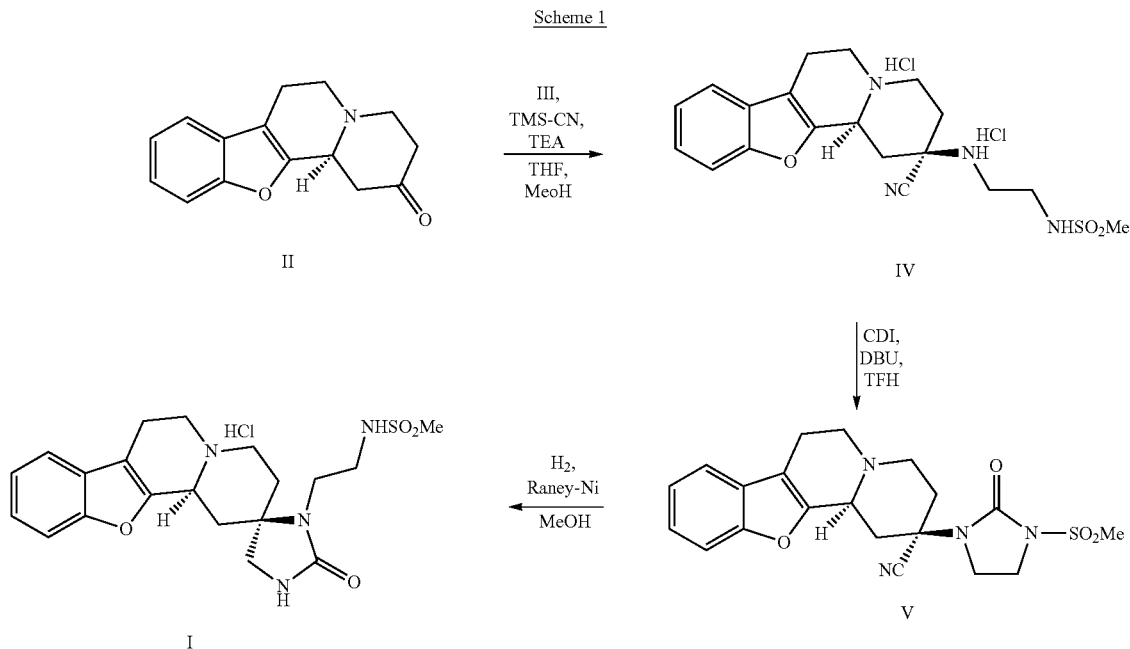

Characteristic features of the invention are presented in the appended claims.

DEFINITIONS

The expression "an agent capable of capturing water molecules" refers here to compounds which are used to remove water from solvents, typically required by chemical reactions that do not tolerate water.

The expression "hydrogen chloride acceptor" refers here to a base capable of capturing hydrogen chloride, preferably a tertiary amine.

DETAILED DESCRIPTION OF THE INVENTION

Figure 1:
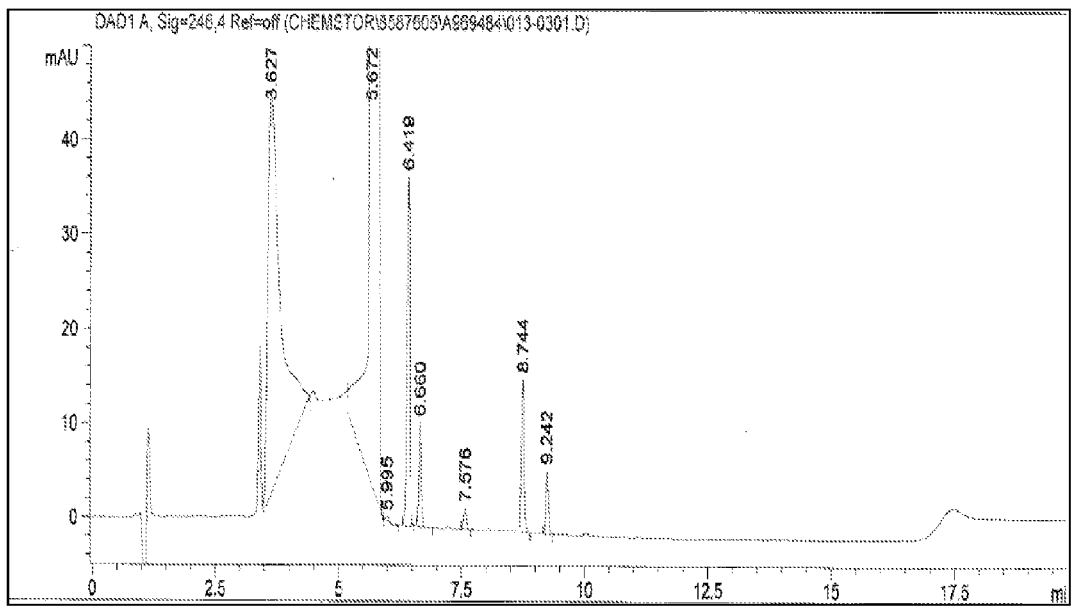
FIG. 1 presents a typical chromatogram of the first intermediate, (2R,12bS)-[2-[(cyano-1,3,4,6,7,12b-hexahydrobenzofuro-[2,3-a]quinolizine-2-yl)-amino]-ethyl]methanesulfon-amide dihydrochloride (compound IV).

It was surprisingly found that significant advantages can be achieved with the process of the invention for the manufacture of N-(2-((2R,12bS)-2'-oxo-1,3,4,6,7,12b-hexahydrospiro[benzofuro[2,3-a]quinolizine-2,4'-imidazolidine]-3'-yl)ethyl)-methanesulfonamide, the advantages being such as improved yields, decreased amounts of impurities and further, the process is suitable for larger industrial scale. In the process the aminocyanation step is carried out without the use of diethyl cyanophosphonate and problems relating to diethyl cyanophosphonate can be avoided.

The process of the invention for the manufacture of N-(2-((2R,12bS)-2'-oxo-1,3,4,6,7,12b-hexahydrospiro[benzofuro[2,3-a]quinolizine-2,4'-imidazolidine]-3'-yl)ethyl)-methanesulfon-amide having the formula I comprises the steps, where in the first step (S)-1,3,4,6,7,12b-hexahydro-2H-benzo[b]furo[2,3-a]quinolizin-2-one of formula II and N-(2-aminoethyl)methanesulfonamide of formula III are contacted with trimethylsilyl cyanide in the presence of an agent capable of capturing water molecules, in an organic solvent, followed by adding hydrogen chloride to obtain (2R,12bS)-[2-[(cyano-1, 3,4,6,7,12b-hexahydrobenzofuro-[2,3-a]quinolizine-2-yl)-amino]ethyl]methanesulfon-amide dihydrochloride, in the second step (2R,12bS)-[2-[(cyano-1,3,4,6,7,12b-hexahydrobenzofuro-[2,3-a]quinolizine-2-yl)-amino]-ethyl]methanesulfonamide dihydrochloride is contacted with 1,1'-carbonyldiimidazole in the presence of a hydrogen chloride acceptor in an organic solvent to obtain (2R,12bS)-1,3,4,6,7,12b-hexahydro-[2,3-methylsulfonyl)-2-oxo-1-imidazolidinyl]-2H-benzo-furo[2,3-a]quinolizine-2-carbonitrile, and in the third step (2R,12bS)-1,3,4,6,7,12b-hexahydro-[2,3-methylsulfonyl)-2-oxo-1-imidazolidinyl]-2H-benzofuro[2,3-a]quinolizine-2-carbonitrile is contacted with hydrogen in the presence of Raney nickel catalyst and sodium methoxide or potassium tert-butoxide in methanol solvent to yield N-(2-((2R,12bS)-2'-oxo-1,3,4,6,7,12b-hexa-hydrospiro-[benzofuro[2,3-a]quinolizine-2,4'-imidazolidine]-3'-yl)ethyl)-methanesulfonamide.

N-(2-((2R,12bS)-2'-oxo-1,3,4,6,7,12b-hexa-hydrospiro-[benzofuro[2,3-a]quinolizine-2,4'-imidazolidine]-3'-yl)ethyl)-methanesulfonamide may be converted to a pharmaceutically acceptable salt, preferably hydrochloride salt, using conventional methods known as such.

First Step

The first step of the process of the invention is an aminocyanation step, where (S)-1,3,4,6,7,12b-hexahydro-2H-benzo[b]furo[2,3-a]quinolizin-2-one (compound II) is allowed react with N-(2-aminoethyl)methanesulfonamide (compound III) in the presence of an agent capable of capturing water molecules, resulting in an imine, which then reacts with trimethylsilyl cyanide to afford α-aminonitrile, which is treated with hydrogen chloride to obtain (2R,12bS)-[2-[(cyano-1,3,4,6,7,12b-hexahydrobenzofuro-[2,3-a]quinolizine-2-yl)-amino]-ethyl]methane-sulfonamide dihydrochloride (compound IV).

In the imine formation reaction water is formed, which rapidly reverses the reaction. The water is captured with the agent capable of capturing water molecules.

The cyanation reaction is very rapid, leading almost exclusively to the desired diastereomer. However, the reaction product epimerizes easily to form an equilibrium mixture of both diastereomers.

In the first step the organic solvent is selected from the group consisting of acetonitrile, dichloromethane, methanol, ethanol, tetrahydrofurane (THF) and mixtures thereof. Optionally an organic base, preferably triethylamine or N,N-diisopropylethylamine, typically in an excess, suitably in an amount of about 1.5 eq., may be added to the solvent for increasing the solubility of compound III. Preferably THF, optionally with triethylamine is used.

An agent capable of capturing water molecules is selected from a group consisting of sodium sulfate, magnesium sulfate, potassium carbonate, typically used in an amount about 3.5 eq., and molecular sieves.

The reaction is carried out at temperature of 10-50° C., preferably at 20-35° C. under normal atmospheric pressure.

After the reaction is completed solids are separated from a liquid fraction and the liquid fraction is treated with hydrogen chloride whereby the first intermediate (compound IV) (2R,12bS)-[2-[(cyano-1,3,4,6,7,12b-hexahydrobenzofuro-[2,3-a]quinolizine-2-yl)-amino]-ethyl]methanesulfon-amide dihydrochloride is precipitated. It may be used as such directly in the second step or it may be dried, suitably at 30-45° C. temperature. Preferably it is used as such directly in the second step, without delays. The precipitated intermediate product is isolated using methods known in the field, such as filtration, centrifuging, etc.

According to one embodiment the starting material (S)-1,3,4,6,7,12b-hexahydro-2H-benzo[b]furo[2,3-a]quinolizin-2-one is added, suitably in an amount of about 1 eq., to reaction mixture containing N-(2-aminoethyl)methanesulfonamide). The reaction mixture is agitated after which an excess, suitably about 1.2 eq. of trimethylsilyl cyanide is added. The reaction time is typically from 0.1-2 hours, after which the solids are removed and work-up is continued without delay.

According to one embodiment the liquid fraction (filtrate and washings) is cooled and (about 3 equivalents of) hydrogen chloride-THF (suitably 20-30% HCl) solution is added to the solution. The precipitation of the first intermediate as its hydrochloride salt improves the purity of the intermediate, as well as the diastrereomeric ratio.

Preferably the pH of the reaction mixture of the firsts step is maintained below 2 after the addition of, hydrogen chloride to the reaction mixture, whereby the stability of (2R,12bS)-[2-[(cyano-1,3,4,6,7,12b-hexahydrobenzofuro-[2,3-a]quinolizine-2-yl)-amino]-ethyl]-methanesulfonamide dihydrochloride is improved.

According to one embodiment the starting material (S)-1,3,4,6,7,12b-hexahydro-2H-benzo[b]furo[2,3-a]quinolizin-2-one (1 eq.) is dissolved in a solvent selected from acetonitrile, dichloromethane, methanol, ethanol, tetrahydrofurane (THF) and mixtures thereof, preferably THF. Then triethylamine (1.5 eq.), sodium sulfate, magnesium sulfate or potassium carbonate (3.5 eq.) or molecular sieve and methanol or ethanol is added to the solution. The temperature of the solution is adjusted to the range of 20-35° C., preferably to 25-33° C., and N-(2-aminoethyl)methanesulfonamide (1 eq.) is added. The reaction mixture is agitated at the temperature of 20-35° C., preferably 25-33° C. for 30-40 min after which trimethylsilyl cyanide (1.2 eq.) is added. The mixture is agitated at 20-35° C. After the reaction is completed (starting material (S)-1,3,4,6,7,12b-hexahydro-2H-benzo[b]furo[2,3-a]quinolizin-2-one is consumed) the reaction mixture is cooled down to −5-+5° C. The cold solution is filtered, and the solid filter cake is rinsed with cold solvent, such as THF. The filtrate and washings are cooled to down to −5-+5° C. and hydrogen chloride-THF (3 eq., 20-30% HCl) solution is slowly added to the solution while keeping the temperature below 5° C. The mixture is agitated at −5-+5° C. and the pH is controlled. If the pH is not below 2 more hydrogen chloride-THF solution is added. The first intermediate (2R,12bS)-[2-[(cyano-1,3,4,6,7,12b-hexahydrobenzofuro-[2,3-a]quinolizine-2-yl)-amino]-ethyl]methanesulfonamide dihydrochloride is precipitated and filtered and washed twice with cold THF. It may be dried (under vacuum at 30-45° C.), or it may be used directly in the second step.

The yields in the first step are typically 74-85%.

Second Step

In the second step the first intermediate (2R,12bS)-[2-[(cyano-1,3,4,6,7,12b-hexahydrobenzofuro-[2,3-a]quinolizine-2-yl)-amino]-ethyl]methanesulfon-amide dihydrochloride (compound IV) reacts with 1,1'-carbonyldiimidazole in the presence of a hydrogen chloride acceptor, whereby a cyclic carbamide, the second intermediate (2R,12bS)-1,3,4,6,7,12b-hexahydro-[2,3-methylsulfonyl)-2-oxo-1-imidazolidinyl]-2H-benzo-furo[2,3-a]quinolizine-2-carbonitrile (compound V) is formed.

1,1'-carbonyldiimidazole is used in molar excess, typically from 3- to 5-fold excess.

The hydrogen chloride acceptor is suitably selected from 1,8-diazabicyclo[2,3-a]undec-7-ene, 1,5-diazabicyclo[4.3.0]non-5-ene, [1,8-bis(dimethylamino)-naphthalene, N,N,N',N'-tetra-methyl-1,8-naphthalene; preferably 1,8-diazabicyclo[2,3-a]undec-7-ene is used.

The reaction is carried out in an organic solvent is selected from the group consisting of dichloromethane, THF, dioxane, dimethylformamide, dimethyl sulfoxide, acetionitrile and combinations thereof.

The reaction is carried out at the temperature of 10-35° C., preferably 15-30° C. under normal atmospheric pressure.

After the reaction is completed, typically after 0.5-10 hours, the reaction mixture is washed with water and brine and an organic phase is separated.

According to one embodiment the organic phase is treated with activated carbon and the second intermediate (compound V) is crystallized from a nonpolar organic solvent, suitably heptane. The crystalline intermediate is suitably dried. Activated carbon treatment improved the subsequent crystallization step significantly.

Preferably the 1,1'-carbonyldiimidazole is added after 1,8-diazabicyclo[5.4.0]undec-7-ene, whereby decomposition caused by (2R,12bS)-[2-[(cyano-1,3,4,6,7,12b-hexahydrobenzofuro-[2,3-a]quinolizine-2-yl)-amino]ethyl]methanesulfonamide hydrochloride can be avoided.

The yield of the second step is typically 75-85%.

Third Step

In the third step of the process the nitrile group in the second intermediate (2R,12bS)-1,3,4,6,7,12b-hexahydro-[2,3-methylsulfonyl)-2-oxo-1-imidazolidinyl]-2H-benzofuro[2,3-a]-quinolizine-2-carbonitrile (compound V) is reduced to a primary amine group, where an intermediate is formed which undergoes spontaneous recyclization to form the final product N-(2-((2R,12bS)-2'-oxo-1,3,4,6,7,12b-hexa-hydrospiro[benzofuro[2,3-a]quinolizine-2,4'-imidazolidine]-3'-yl)ethyl)-methanesulfonamide (compound I).

The third step is carried out in the presence of sodium methoxide or potassium tert-butoxide, preferably sodium methoxide solution is used.

The third step is carried out at a temperature of 45-66° C., preferably at 55-60° C.

The third step is carried out under hydrogen pressure of 1-10 bar, preferably 2-5 bar.

The Raney-nickel catalyst is preferably added as an aqueous slurry to the reaction mixture, preferably as a 40-60 wt % slurry.

After the reaction is completed, typically after 3-20 hours, a liquid fraction is separated and subjected to work-up whereby the product N-(2-((2R,12bS)-2'-oxo-1,3,4,6,7,12b-hexahydrospiro[benzofuro[2,3-a]quinolizine-2,4'-imidazolidine]-3'-yl)ethyl)-methane-sulfonamide is obtained.

Preferably the product N-(2-((2R,12bS)-2'-oxo-1,3,4,6,7,12b-hexahydrospiro[benzofuro-[2,3-a]quinolizine-2,4'-imidazolidine]-3'-yl)ethyl)methanesulfonamide is converted to its pharmaceutically acceptable salt, preferably hydrochloride. Suitably the product is dissolved in THF and then hydrogen chloride-isopropanol solution is added whereby the N-(2-((2R,12bS)-2'-oxo-1,3,4,6,7,12b-hexahydrospiro[benzofuro-[2,3-a]quinolizine-2,4'-imida-zolidine]-3'-yl)ethyl)methanesulfonamide hydrochloride product is formed. After work-up a dry powder is obtained.

Preferably the pharmaceutically acceptable salt of N-(2-((2R,12bS)-2'-oxo-1,3,4,6,7,12b-hexahydrospiro[benzofuro-[2,3-a]quinolizine-2,4'-imidazolidine]-3'-yl)ethyl)methane-sulfonamide, preferably hydrochloride, is recrystallized to remove impurities such as the undesired diastereomer. The recrystallization is carried out preferably using methanol.

The yield of the third step is typically 65-75%. The purity of the final product is typically 99.8-100%.

The starting materials (S)-1,3,4,6,7,12b-hexahydro-2H-benzo[b]furo[2,3-a]quinolizin-2-one (compound II) and N-(2-aminoethyl)methanesulfonamide (compound III) can be obtained using the methods described in U.S. Pat. No. 4,942,235, U.S. Pat. No. 4,831,035 and EP 0259092.

The process of the invention has several advantages. Use of diethylcyanophosphonate, which is expensive and has poor availability, can be avoided, whereby also formation of phosphonate salts can be avoided, as well as long reactions times and complicated measures in the isolation of the intermediate.

Trimethylsilyl cyanide is easily available and cheap compound. The reaction with trimethylsilyl cyanide is very fast whereby very low amounts of the undesired diastereomer may be formed, yields are improved and the isolation of the intermediate is easy. Removal of trimethylsilyl cyanide residues is easier if compared to phosphonate salts.

Thus also the overall yield of the process of the invention and purity of the final product are improved.

Examples

The invention will now be illustrated with the following examples and with reference to the drawings.

Example 1

First Step

Manufacture of (2R,12bS)-[2-[(cyano-1,3,4,6,7,12b-hexahydrobenzofuro-[2,3-a]quinolizine-2-yl)-amino]ethyl]methanesulfonamide dihydrochloride (IV) on Laboratory Scale 20 g (0.083 mol) of (S)-1,3,4,6,7,12b-hexahydro-2H-benzo[b]furo[2,3-a]quinolizin-2-one was dissolved in 1500 ml of THF after which triethylamine 16.8 ml (0.124 mol), sodium sulfate 41.3 g (0.291 mol), and 300 ml of methanol were added to the solution. The temperature of the solution was adjusted to 30° C. and N-(2-aminoethyl)-methanesulfonamide 21.7 g (0.124 mol) was added. The reaction mixture was stirred at 30° C. for 30 min after which trimethylsilyl cyanide 9.7 g (0.099 mol) was added. The mixture was stirred at 30° C. and the reaction was monitored by GC. When all (S)-1,3,4,6,7,12b-hexahydro-2H-benzo[b]furo[2,3-a]quinolizin-2-one was consumed the reaction mixture was cooled down to 0±5° C. The reaction typically took 1-1.5 h after the trimethylsilyl cyanide addition. The cold solution was filtered to remove the sodium sulfate, which was rinsed with 100 ml of cold THF. The combined filtrate and washings were cooled to 0±5° C. and 3 equivalents of ~20 wt % hydrogen chloride-THF solution (0.249 mol) was slowly added to the solution while keeping the temperature below 5° C. The mixture was stirred for 5-10 min at 0±5° C. and pH was measured to assure that the solution is acidic (pH 1-2). The product was filtered of and rinsed twice with 100 ml of cold THF. The product was dried under vacuum at 30° C. overnight. The yield was typically in the range 75-85%.

Example 2

First Step

Manufacture of (2R,12bS)-[2-[(cyano-1,3,4,6,7,12b-hexahydrobenzofuro-[2,3-a]quinolizine-2-yl)-amino]ethyl]methanesulfonamide dihydrochloride (IV) on Larger Scale The starting materials 5.0 kg (20.7 mol) of (S)-1,3,4,6,7,12b-hexahydro-2H-benzo[b]furo[2,3-a]quinolizin-2-one, 10.0 kg (70.4 mol) of sodium sulfate, and 366 kg of THF were charged to the reactor, followed by the addition of 3.1 kg (30.6 mol) of triethylamine and 56 kg of methanol. The temperature of the solution was raised to 25° C., after which 5.4 kg (30.9 mol) of N-(2-aminoethyl)methanesulfonamide was charged to the reactor. The reaction mixture was agitated at 30° C. for 30 minutes prior to the addition of 2.5 kg (25.2 mol) trimethylsilyl cyanide and 19 kg of methanol. The reaction was left to proceed at 30° C. for 1 hour. After completion the reaction mixture was cooled to 0° C. and filtered. To the cold solution 9.4 kg of a 24% hydrogen chloride/THF solution was added. The reaction mixture was agitated at 0° C. for 30 minutes and the pH was measured to assure that the pH is below 2. The product was filtered of and washed two times with 19 kg of cold THF. The filtered wet product was used as such in the second step.

A typical chromatogram of (2R,12bS)-[2-[(cyano-1,3,4,6,7,12b-hexahydrobenzofuro-[2,3-a]quinolizine-2-yl)-amino]-ethyl]methanesulfonamide dihydrochloride (RT 5.67 min) obtained in the first step is shown in FIG. 1. As can be seen from the chromatogram, the compound is not very stable but decomposes readily back to (S)-1,3,4,6,7,12b-hexahydro-2H-benzo[b]furo[2,3-a]quinolizin-2-one (RT 3.63 min) during the analysis.

Example 3

Second step

Manufacture of (2R,12bS)-1,3,4,6,7,12b-hexahydro-2-[3-(methylsulfonyl)-2-oxo-1-imidazolidinyl]-2H-benzofuro[2,3-a]quinolizine-2-carbonitrile (V)

1,1'-carbonyldiimidazole 21.8 g (0.134 mol) was dissolved in 620 ml of dichloromethane and the reaction vessel was flushed with a gentle stream of nitrogen. To the solution 20.6 ml (0.138 mol) of 1,8-diazabicyclo[5.4.0]undec-7-ene and 31 g (0.067 mol) of (2R,12bS)-[2-[(cyano-1,3,4,6,7,12b-hexahydrobenzofuro-[2,3-a]quinolizine-2-yl)-amino]-ethyl]-methanesulfonamide dihydrochloride were added. The reaction mixture was stirred at room temperature and monitored by HPLC. When the reaction was finished the reaction mixture was washed twice with water (200 ml) and twice with brine (100 ml) after which layers were separated and the organic layer was treated with 1.5 g of activated carbon (Norit® SX1) at room temperature. The mixture was filtered and the carbon was rinsed with 50 ml of dichloromethane. The product solution was concentrated to half of its mass and the temperature of it was adjusted to 30° C. Heptane (130 ml) was slowly added to the concentrated solution under constant stirring. The solution was seeded with a small amount of (2R,12bS)-1,3,4,6,7,12b-hexahydro-2-[3-(methylsulfonyl)-2-oxo-1-imidazolidinyl]-2H-benzofuro[2,3-a]quinolizine-2-carbonitrile, followed by a slow addition of another 800 ml of heptane (the total time for the heptane addition was approximately 6 h). The mixture was cooled down to 0-5° C. and stirred for 1-2 h. The crystals were filtered off and rinsed with 280 ml of heptane. The product was dried under vacuum at 40° C. overnight. The yield was typically in the range of 80-85% and the HPLC purity 94-98%.

Figure 2:
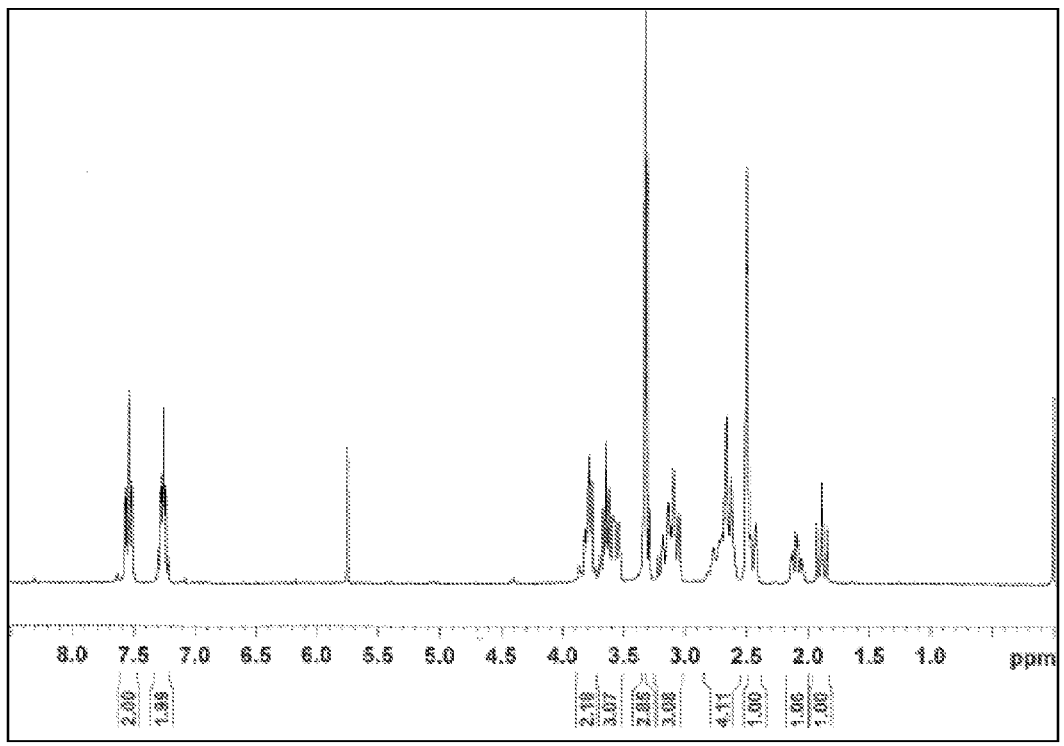
FIG. 2 presents a typical $^1$H NMR spectra of the second intermediate (2R,12bS)-1,3,4,6,7,12b-hexahydro-[2,3-methylsulfonyl)-2-oxo-1-imidazolidinyl]-2H-benzo-furo[2,3-a]-quinolizine-2-carbonitrile (compound V).

A typical $^1$H NMR spectrum of the obtained (2R,12bS)-1,3,4,6,7,12b-hexahydro-2-[3-(methylsulfonyl)-2-oxo-1-imidazolidinyl]-2H-benzofuro[2,3-a]quinolizine-2-carbonitrile is presented in FIG. 2. $^1$H NMR (DMSO-d6, 300 MHz): δ 7.52-7.58 (m, 2H), 7.25-7.29 (m, 2H), 3.77-3.82 (m, 2H), 3.54-3.68 (m, 3H), 3.33 (s, 3H), 3.05-3.19 (m, 3H), 2.60-2.77 (m, 4H), 2.42-2.47 (dd, 1H, 3=12.9, 2.3 Hz), 2.04-2.14 (dt, 1H, J=12.8, 4.3 Hz), 1.89 (t, 1H, J=12.8 Hz).

Figure 3:
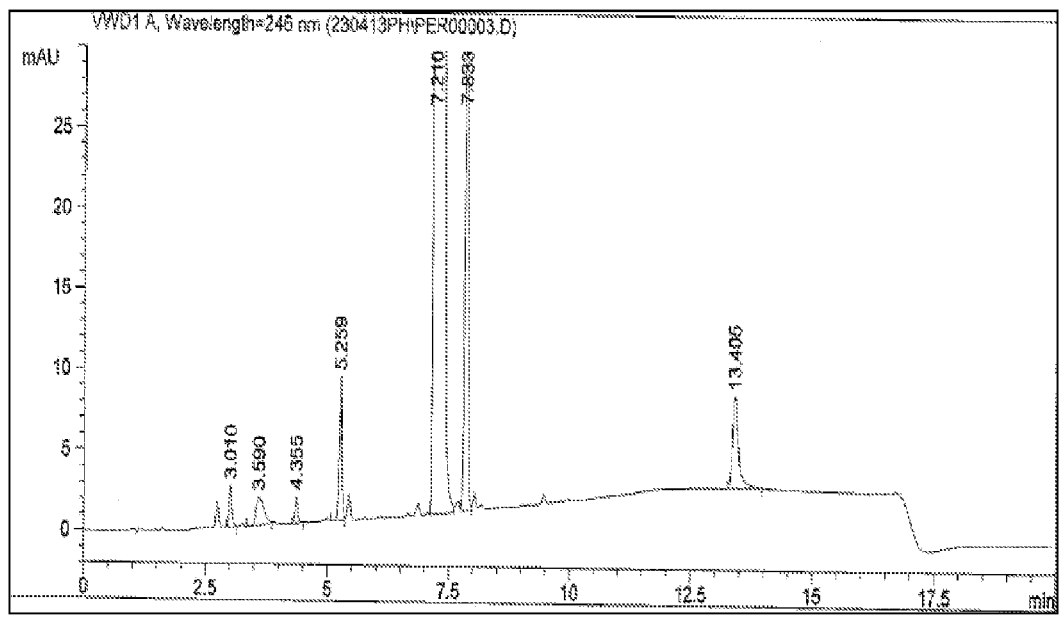
FIG. 3 shows a typical HPLC chromatogram of the second intermediate (2R,12bS)-1,3,4,6,7,12b-hexahydro-[2,3-methylsulfonyl)-2-oxo-1-imidazolidinyl]-2H-benzo-furo[2,3-a]-quinolizine-2-carbonitrile (compound V).

A typical HPLC chromatogram of (2R,12bS)-1,3,4,6,7,12b-hexahydro-2-[3-(methylsulfonyl)-2-oxo-1-imidazolidinyl]-2H-benzofuro[2,3-a]quinolizine-2-carbonitrile, (RT 7.21 min) and purity 97.1% is presented in FIG. 3.

Example 4

Third step

Manufacture of N-(2-((2R,12bS)-2'-oxo-1,3,4,6,7,12b-hexahydrospiro[benzofuro[2,3-a]quinolizine-2,4'-imidazolidine]-3'-yl)ethyl)-methanesulfonamide hydrochloride 2 g (0.005 mol) of (2R,12bS)-1,3,4,6,7,12b-hexahydro-2-[3-(methylsulfonyl)-2-oxo-1-imidazolidinyl]-2H-benzofuro[2,3-a]quinolizine-2-carbonitrile was dissolved in 200 ml of methanol and 1.9 ml (0.010 mol) of 30% sodium methylate was added to the solution after which the reactor was flushed with nitrogen. 3 g (150 wt %) of Raney nickel catalyst was added to the solution as a 50% slurry in water. The reactor was evacuated and flushed with hydrogen gas three times before finally adjusting the hydrogen pressure to 2.5-3 bar. The reaction mixture was heated to 55-60° C. and stirred at this temperature until the reaction had run to completion. The reaction was monitored by HPLC. After the reaction was completed the reaction mixture was cooled down to room temperature and the hydrogen pressure was released. The catalyst was removed by filtration under a gentle stream of nitrogen and rinsed with 100 ml of methanol. The combined filtrate and methanol used for the rinsing of the catalyst was concentrated to almost dryness. The residue was dissolved in 100 ml of dichloromethane and washed with 24 ml of saturated sodium bicarbonate solution. The organic phase was separated and concentrated to almost dryness after which the residue was dissolved in 30 ml of THF. The solution was heated to 40° C. and 3.5 g (2 eq.) of a 10% hydrogen chloride-isopropanol solution was added drop-wise under constant stirring. The mixture was stirred at 40° C. for 0.5-1 h and then cooled to 0-5° C. and stirred for another 0.5-1 h. The product was filtered off and rinsed twice with 5 ml of THF. The product N-(2-((2R,12bS)-2'-oxo-1,3,4,6,7,12b-hexahydrospiro-[benzofuro[2,3-a]quinolizine-2,4'-imidazo-lidine]-3'-yl)ethyl)-methanesulfonamide hydrochloride was dried under vacuum at 50° C. overnight. The yield was about 80%.

Figure 4:
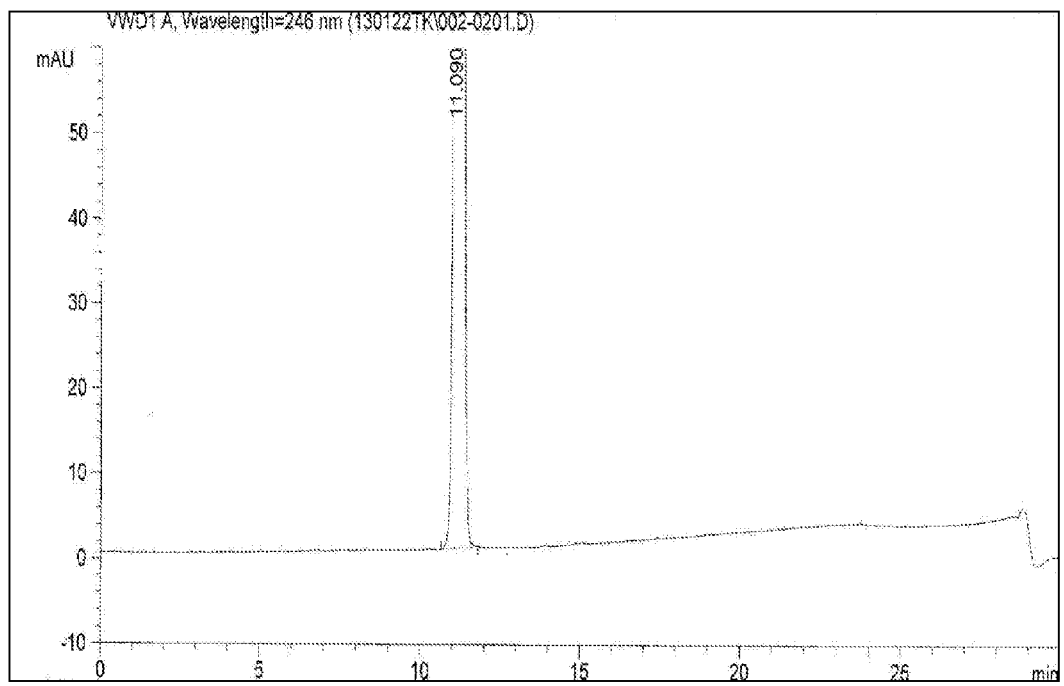
FIG. 4 shows a typical HPLC chromatogram of the final product of N-(2-((2R,12bS)-2'-oxo-1,3,4,6,7,12b-hexahydrospiro[benzofuro[2,3-a]quinolizine-2,4'-imidazolidine]-3'-yl)-ethyl)-methanesulfonamide.

Recrystallization of N-(2-((2R,12bS)-2'-oxo-1,3,4,6,7,12b-hexahydrospiro-[benzofuro[2,3-a]quinolizine-2,4'-imidazolidine]-3'-yl)ethyl)-methanesulfonamide hydrochloride 20 g (0.044 mol) of N-(2-((2R,12bS)-2'-oxo-1,3,4,6,7,12b-hexahydrospiro-[benzo-furo[2,3-a]quinolizine-2,4'-imidazolidine]-3'-yl)ethyl)-methanesulfonamide hydrochloride was dissolved in 1700 ml of refluxing methanol. The warm solution was filtered and concentrated by distillation under atmospheric pressure until 70% of the methanol was removed. After the distillation the solution was cooled down to 5° C. during 8 hours, and then stirred at 5° C. for 3 hours. The product was filtered and washed twice with 25 ml of cold methanol. The product was dried under vacuum using a heating ramp from 50° C. to 100° C., and then milled. The yield of recrystallization was typically 70%. HPLC chromatogram of the final product N-(2-((2R,12bS)-2'-oxo-1,3,4,6,7,12b-hexa-hydrospiro[benzofuro[2,3-a]quinolizine-2,4'-imidazolidine]-3'-yl)ethyl)-methanesulfon-amide hydrochloride is presented in FIG. 4, where the purity was 100%.

Example 5

Manufacture of starting material N-(2-aminoethyl)methanesulfonamide hydrochloride 40 g (0.392 mol) of N-(2-aminoethyl)acetamide and 59.4 g (0.587 mol) of triethylamine were dissolved in 600 ml of dichloromethane. The solution was cooled down to 0 . . . +5° C. after which 67.2 g (0.587 mol) of methanesulfonyl chloride was added during a period of 1-1.5 h under continuous stirring, while keeping the temperature not higher than +5° C. during the addition. When the addition was finished the reaction mixture was stirred for another 3 hours while the temperature was allowed to rise to room temperature. After the reaction was completed the reaction mixture was evaporated to dryness. Dichloromethane saturated with ammonia (2000 ml) was added to the evaporation residue and the mixture was triturated for 15-30 min at room temperature. The formed precipitate was filtered off and the filtrate was evaporated to dryness. The evaporation residue was dissolved in 6 M hydrochloric acid (980 ml). The solution was heated to reflux (approx. 110° C.) and stirred at this temperature for 2 h. When the reaction was finished the reaction mixture was allowed to cool down to 60° C. and then evaporated to dryness under reduced pressure. The evaporation residue was dissolved in 460 ml of methanol and then again evaporated to dryness to remove traces of water. The residue was dissolved in another 460 ml of methanol after which 3 g of –activated carbon (Norit® SX1) was added. The mixture was stirred for 15 min at 30° C., and filtered. The methanol solution was concentrated to about one third of the original mass. The crystallization was initiated by adding 85 ml of dichloromethane during 1 h under constant stirring. The solution was seeded by adding approximately 200 mg of seeding material N-(2-aminoethyl)methanesulfonamide hydrochloride. The solution was stirred for 15 min after which slow dichloromethane addition (1600 ml) was continued over a period of 6 hours under constant stirring. The mixture was cooled to 5° C. and stirred at this temperature for another 3 hours. The crystals were filtered and washed with 2×70 ml of cold acetone. The product was dried under vacuum at 30° C. overnight. The yield was typically in the range of 70-80%.

The present invention has been described herein with reference to specific embodiments. It is, however clear to those skilled in the art that the invention may be varied within the bounds of the claims.

The invention claimed is:

1. A process for the preparation of N-(2-((2R,12bS)-2'-oxo-1,3,4,6,7,12b-hexa-hydrospiro[benzofuro[2,3-a]quinolizine-2,4'-imidazolidine]-3'-yl)ethyl)-methane-sulfonamide, wherein the process comprises the following steps:
in the first step (S)-1,3,4,6,7,12b-hexahydro-2H-benzo[b]furo[2,3-a]quinolizin-2-one of formula II:

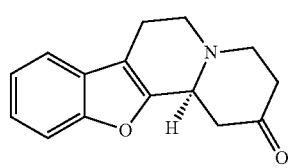

(II)

and N-(2-aminoethyl)methanesulfonamide of formula III:

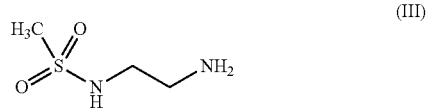

(III)

are contacted with trimethylsilyl cyanide in the presence of an agent capable of capturing water molecules, in an organic solvent, followed by adding hydrogen chloride to obtain (2R,12bS)-[2-[(cyano-1,3,4,6,7,12b-hexahydrobenzofuro-[2,3-a]quinolizine-2-yl)-amino]ethyl]methanesulfonamide dihydrochloride,
in the second step (2R,12bS)-[2-[(cyano-1,3,4,6,7,12b-hexahydrobenzofuro-[2,3-a]quinolizine-2-yl)-amino]-ethyl]methanesulfonamide dihydrochloride is contacted with 1,1'-carbonyldiimidazole in the presence of a hydrogen chloride acceptor in an organic solvent to obtain (2R,12bS)-1,3,4,6,7,12b-hexahydro-[2,3-methylsulfonyl)-2-oxo-1-imidazolidinyl]-2H-benzo-furo[2,3-a]quinolizine-2-carbonitrile, and
in the third step (2R,12bS)-1,3,4,6,7,12b-hexahydro-[2,3-methylsulfonyl)-2-oxo-1-imidazolidinyl]-2H-benzo-furo[2,3-a]quinolizine-2-carbonitrile is contacted with hydrogen in the presence of Raney nickel catalyst and sodium methoxide or potassium tert-butoxide in methanol solvent to yield N-(2-((2R,12bS)-2'-oxo-1,3,4,6,7,12b-hexahydrospiro[benzofuro[2,3-a]quinolizine-2,4'-imidazolidine]-3'-yl)ethyl)-methanesulfonamide.

2. The process according to claim 1, wherein in the first step the agent capable of capturing water molecules is selected from a group consisting of sodium sulfate, magnesium sulfate, potassium carbonate and molecular sieves.

3. The process according to claim 1, wherein in the first step the organic solvent is selected from the group consisting of acetonitrile, dichloromethane, methanol, ethanol, tetrahydrofuran and mixtures thereof.

4. The process according to claim 1, wherein in the first step triethylamine is added to the solvent.

5. The process according to claim 1, wherein in the first step temperature is 0-50° C.

6. The process according to claim 1, wherein in the first step the pH is maintained below 2 during the addition of hydrogen chloride.

7. The process according to claim 1, wherein in the second step the hydrogen chloride acceptor is selected from 1,8-diazabicyclo[2,3-a]undec-7-ene, 1,5-diazabicyclo[4.3.0]non-5-ene, [1,8-bis(dimethylamino)-naphthalene and N,N,N',N'-tetra-methyl-1,8-naphthalene.

8. The process according to claim 1, wherein in the second step the temperature is 10-35° C.

9. The process according to claim 7, wherein in the second step 1,1'-carbonyldiimidazole is added after 1,8-diazabicyclo[5.4.0]undec-7-ene.

10. The process according to claim 1, wherein the third step is carried out at a temperature of 45-66° C.

11. The process according to claim 1, wherein the third step is carried out under hydrogen pressure of 1-10 bar.

12. The process according to claim 1, wherein N-(2-((2R,12bS)-2'-oxo-1,3,4,6,7,12b-hexahydrospiro[benzofuro-[2,3-a]quinolizine-2,4'-imidazolidine]-3'-yl)ethyl)methanesulfonamide is converted to its pharmaceutically acceptable salt.

13. The process according to claim 12, wherein the pharmaceutically acceptable salt of N-(2-((2R,12bS)-2'-oxo-1,3,4,6,7,12b-hexahydrospiro-[benzofuro-[2,3-a]quinolizine-2, 4'-imidazolidine]-3'-yl)ethyl)methanesulfonamide is recrystallized using methanol.

14. The process according to claim 2, wherein in the first step the organic solvent is selected from the group consisting of acetonitrile, dichloromethane, methanol, ethanol, tetrahydrofuran and mixtures thereof.

15. The process according to claim 2, wherein in the first step triethylamine is added to the solvent.

16. The process according to claim 3, wherein in the first step triethylamine is added to the solvent.

17. The process according to claim 1, wherein in the first step temperature is 20-35° C.

18. The process according to claim 2, wherein in the first step temperature is 0-50° C.

19. The process according to claim 7, wherein in the second step the hydrogen chloride acceptor is 1,8-diazabicyclo[2,3-a]undec-7-ene.

20. The process according to claim 2, wherein in the first step the pH is maintained below 2 during the addition of hydrogen chloride.

* * * * *